United States Patent [19]

Kurtz

[11] Patent Number: 4,470,941

[45] Date of Patent: Sep. 11, 1984

[54] PREPARATION OF COMPOSITE SURGICAL SUTURES

[75] Inventor: Leonard D. Kurtz, Woodmere, N.Y.

[73] Assignee: BioResearch Inc., Farmingdale, N.Y.

[21] Appl. No.: 384,245

[22] Filed: Jun. 2, 1982

[51] Int. Cl.³ .............................................. B29B 3/02
[52] U.S. Cl. ..................... 264/136; 128/335.5;
264/108; 264/134; 264/171; 264/174;
264/288.8; 264/290.5; 264/345
[58] Field of Search ...................... 428/397, 375, 372;
425/113, 192 R; 264/174, 562, 108, 288.8,
134-137, 345, 210.8, 290.5, 171, 210.7;
128/335.5

[56] References Cited

U.S. PATENT DOCUMENTS

| 2,962,756 | 12/1960 | Biche et al. | 425/113 |
|---|---|---|---|
| 3,322,125 | 5/1967 | Kurtz | 128/335.5 |
| 3,379,552 | 4/1968 | Kurtz | 117/7 |
| 3,449,187 | 6/1969 | Bobkowicz | 264/258 |
| 3,461,197 | 8/1969 | Lemelson | 425/113 |
| 3,494,118 | 2/1970 | Bobkowicz et al. | 264/103 |
| 3,527,650 | 9/1970 | Block | 128/335.5 |
| 3,557,403 | 1/1971 | Lemelson | 425/113 |
| 3,630,205 | 12/1971 | Listner | 264/210.8 |
| 3,687,776 | 8/1972 | Allard et al. | 264/258 |
| 3,740,304 | 6/1973 | Okumaro et al. | 428/397 |
| 3,844,097 | 10/1974 | Bobkowicz et al. | 264/103 |
| 3,924,396 | 12/1975 | Bobkowicz | 264/258 |
| 3,944,459 | 3/1976 | Skobel | 425/113 |
| 3,946,097 | 3/1976 | Takahashi et al. | 264/562 |
| 3,987,612 | 10/1976 | Bobkowicz | 264/103 |
| 4,043,720 | 8/1977 | Mercer | 425/113 |
| 4,046,103 | 9/1977 | Yakuboff | 425/113 |
| 4,068,615 | 1/1978 | LeNir | 425/113 |
| 4,093,693 | 6/1978 | Lemelson | 264/171 |
| 4,127,370 | 11/1978 | Jackson | 425/113 |
| 4,303,734 | 12/1981 | Sullivan | 425/192 R |

FOREIGN PATENT DOCUMENTS

| 745490 | 2/1970 | Belgium | 428/372 |
|---|---|---|---|
| 1211737 | 11/1970 | United Kingdom | 264/108 |

Primary Examiner—Jeffery Thurlow
Attorney, Agent, or Firm—Larson and Taylor

[57] ABSTRACT

Composite sutures of dissimilar synthetic polymer materials are prepared by forming a thread comprised of a plurality of fibers of a first synthetic polymer, said thread further comprising a second synthetic polymer in intimate association with and present uniformily along the length of said first synthetic polymer, softening the second synthetic polymer to cause it to flow, applying pressure to the softened polymer to redistribute it throughout the plurality of fibers, and into the interstices thereof and sterilizing the thread to form a suture thereof.

33 Claims, 2 Drawing Figures

PREPARATION OF COMPOSITE SURGICAL SUTURES

BACKGROUND OF THE INVENTION

1. Field of the Invention

This invention relates to a method for preparing composite surgical sutures. More particularly, the invention is directed to methods by which composite sutures of improved lateral strength are obtained.

2. Brief Description of the Prior Art

Composite sutures offer a number of advantages recognized by the prior art. For instance, there are many synthetic fibers which per se are unsuitable for use in sutures because they lack one or more of the properties required in surgical sutures but which possess, nevertheless, certain other properties considered desirable in sutures. By way of example, fibers drawn from many synthetic polymers are too stiff and do not satisfy the knottability requirements of sutures. At the same time these synthetic polymers may possess a tensile strength that renders their use in sutures highly desirable. It is not surprising, therefore, that there have been numerous attempts to combine the best properties of different synthetic materials by compositing them in various ways. These compositing attempts have not been without shortcomings, however.

The principal difficulties involved in the preparation of composite sutures have resided in the fact that polymers whose properties render them desirable for compositing often lack cohesiveness for one another and are otherwise unable to adhere to each other. Many have attempted to remedy these problems by resorting to chemical adhesion through reactive groups provided the polymer components and/or chemical additives to assist in the binding of one polymer component to the other. These techniques, in addition to being costly have in large part proved unsuccessful.

Other attempts to integrate multi-components strands in the production of strings for athletic rackets has been described, for example, in U.S. Pat. No. 4,275,117 to Steven J. Crandall and involves subjecting a fibrous strand composed of fibrous materials having differing melting points to heating conditions sufficient to melt some but not all of the fibrous materials. While perhaps satisfactory for tennis string production or the like, this method of forming composites, as in the case of other aforementioned prior art methods, provides unsatisfactory surgical sutures in that they are found to possess poor lateral strength manifested by a lack of stability against abrasion, kinking and fibrillation during knotting.

Accordingly, it is an object of the present invention to provide a method whereby composite sutures of synthetic polymers having improved lateral strength, that is, composite sutures stabilized against abrasion, kinking and/or fibrillation during knotting are obtained.

Yet another object of the invention is to provide a method of enabling preparation of composite sutures whose surface characteristics, tensile strength and/or knot strength can be tailored to desired specifications.

A further object of the invention is to provide a method of preparing a composite suture whereby one synthetic polymer is tenaciously anchored to the other without the use of chemical adhesion, chemically reactive groups or additives to bind one polymer to the other.

A still further object of the invention is to provide a method for composite suture preparation which enables the use of synthetic fibers heretofore unsuitable for use in suture manufacture.

Another subject of the invention is to provide a method of manufacturing a composite suture having monofilament characteristics which is free of flaking on its outer surface and which retains in large part the flexibility, knottability, knot retention and tensile strength that characterizes multifilament sutures.

SUMMARY OF THE INVENTION

These and other objects of the invention are obtained by forming a thread having interstices therein, comprised of a plurality of fibers of a first synthetic polymer, said thread further comprising a second synthetic polymer in intimate association with and present along the length of at least one of said plurality of fibers, softening said second synthetic polymer to cause flow thereof, applying sufficient pressure to the softened polymer for a time sufficient to redistribute it throughout the plurality of fibers of said first synthetic polymer and into the interstices thereof.

Absolutely essential to the construction of the composite sutures is the pressure step of the method for without it composite sutures having acceptable lateral strength are not obtained. The pressure can be applied to the softened polymer component of the thread in any suitable way with the only proviso being that sufficient pressure be used for a time sufficient to redistribute the softened polymer throughout the fibers of the first synthetic polymer and substantially fill the voids in the thread. According to one preferred embodiment of the invention the pressure is applied by placing the thread under tension during the softening operation. Another preferred method by which the pressure can be applied in the method of the invention is to pass the thread immediately after the softening operation through a compression die having a reduced diameter relative to that of the diameter of the thread so that the necessary pressure can be applied. Although unnecessary, it is preferred in the latter case to use a compression die heated to above the melting point of the polymer component softened. If desired, both forms of pressure application can be utilized as by first effecting the pressure by placing the thread under tension followed by passing the thread through the compression die of reduced diameter.

Since the thread is under pressure, the softened dissimilar polymer exudes into and through interstices existing in the plurality of unsoftened fibers, substantially filling same and forming an internal cast within the matrix of unsoftened fibers upon resolidification. The internal cast of the softened polymer may be continuous or discontinuous and will appear in cross-section in the composite suture as a homogeneous, solid phase throughout the plurality of unsoftened fibers. In most instances, it will be preferred to use an amount of softened polymer sufficient to form upon redistribution throughout the plurality of fibers of the unsoftened synthetic fiber an external cast extending continuously throughout the thread.

Also, where enough of the polymer component softened is present, the liquified polymer exudes through the interstices of the unsoftened fibers and onto the surface of the thread so as to form a coating thereon.

In all instances, however, the internal cast formed within the matrix of unsoftened fibers serves as a tenacious "anchor" onto which additional softened synthetic polymer can be secured as by coating, if desired.

Composite sutures prepared by the present invention having coatings of the exuded synthetic polymer component are preferably smoothed, for instance, by passing them through a heated smoothing die. The smoothed composite thread may then be sterilized if desired to form a surgical suture. In many instances, it may be necessary to further coat the smoothed composite with additional similar synthetic polymer as by extrusion or melt coating to seal and further strengthen the composite thread formed. In addition where the thread is in braided form, subsequent coating tends to eliminate any undulating effect that results as a consequence of the braid and provide a flexible, composite polyfilamentous composite suture having a monofilament-like structure exhibiting improved knottability and knot retention. The improvement in knottability and knot retention characteristics is obtained by virtue of the fact that when a knot is "thrown" and tied down, the suture undergoes a marked deformation in the knot due to the "hills and dales" of the underlying thread.

DETAILED DESCRIPTION OF THE INVENTION

Figure 1:
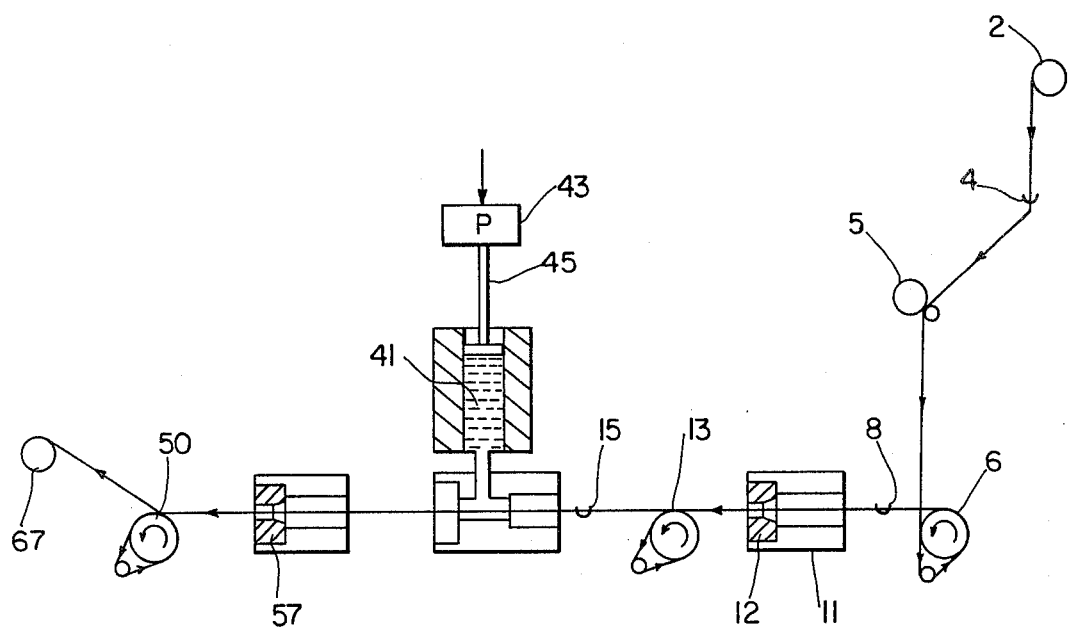

By the term "softening" as used herein and the appended claims is meant any operation by which one of the synthetic polymer components of the thread treated but not the other is brought from a solid or highly viscous state to a viscosity causing flow of the synthetic polymer under the prevailing conditions. This "softening" can be achieved by a variety of ways such as by the use of heat, selective solvents, high energy sources such as lasers, etc. Other suitable ways of effecting the softening will readily come to the mind of those of ordinary skill in this art.

In the aspect of the invention wherein the softening is induced by heating, the thread, comprised of a matrix of a plurality of fibers of a first synthetic polymer and a second solid, dissimilar synthetic polymer having a melting point lower than the melting point of said first synthetic polymer is heated at a elevated temperature sufficient to melt and liquify the dissimilar synthetic polymer, to a viscosity permitting flow throughout the matrix.

Similarly, where the "softening" is induced by a solvent, the thread of dissimilar synthetic polymer components is contacted at a temperature and with a solvent capable of solubilizing or softening the second synthetic polymer but not the first at the contact temperature. The contact time will vary depending principally upon the particular synthetic polymer to be softened and the solvent and contact temperature employed. In all instances, however, the contact time will be sufficient to cause one of the synthetic polymer components to flow, that is, to reduce the viscosity of the polymer to where it flows under the external pressure applied according to the invention and through the remaining, or unsoftened synthetic fibers so as to fill the voids or interstices therein. There is thus formed an internal cast throughout the thread which is dried to resolidify the exuded softened polymer component.

The thread softened in accordance with the present invention can assume a variety of structures and the polymer component to be softened can be present during the softening in any desired form such as a film or fiber, or as a coating on the polymer not softened. In one embodiment, for example, the thread is comprised of lower melting point synthetic polymer fibers in a plied, twisted, braided or commingled construction with synthetic polymer fibers of higher melting point. A preferred form of this embodiment involves heating under tension a thread comprised of a cover of a polyfilamentous synthetic polymer surrounding a core of at least one but preferably a plurality of fibers of a dissimilar synthetic polymer having a lower melting point than the synthetic polymer of said cover.

Alternatively, the thread to be heated pursuant to the present invention can comprise, at least in part, a plurality of synthetic polymer fibers coated with a dissimilar synthetic polymer having a melting point lower than that of the synthetic polymer fiber substrate, which coated fibers are in a plied, twisted, braided, commingled or simply aligned construction.

The proportions of lower melting point synthetic polymer component to higher melting point synthetic polymer component employed in the thread heated in accordance with the invention will vary depending principally upon the particular components selected, whether or not a continuous or discontinuous internal cast is desired and whether or not a composite coated with melted components is the intended product. In all instances, however, the component melted should be present in amounts at least sufficient to provide adequate anchoring sites for additional like synthetic polymer material that may be subsequently applied as by coating to the composite thread formed.

In general, the ratio of higher melting point synthetic polymer material to lower melting point synthetic polymer material in the initial thread required to achieve adequate anchoring sites is at least 0.5:1 on a volume bases. Ratios of melted to unmelted synthetic polymers in excess of 1:10 up to 2:1 are generally required, however, if it is desired to not only fill all the interstices of the thread but to coat the thread as well. Proportions in excess of about 12:1, can create processing difficulties due to thread line non-uniformities.

Heating of the precursor thread of multiple synthetic polymer components to temperatures above the melting point of one of the synthetic components can be conducted in any suitable manner as by passing it through a suitable oven preferably under an inert gas such as nitrogen. As the composite thread passes through the oven, the synthetic component of lower melting point melts and under the applied pressure exudes through the voids present in the plurality of higher melting fibers remaining leaving them substantially filled. Preferably the softened polymer exudes onto the surface under the tension applied.

Any excess melted synthetic polymer can then be trimmed off manually but it is preferred that the thread structure thus formed be passed through a heated die which trims nubs from the thread and otherwise smooths the external surface of the thread. If the thread thus formed is to be coated, it is important to select a die in this operation which provides a precoated yarn that is at least 20–40 microns thinner than the suture class limits in order to leave room for the coating. Again, it is preferred that this operation be conducted under an inert gas such as nitrogen. Stretch may also be applied during the smoothing operation. The thread may be passed through the heating oven and/or smoothing die as many times as is necessary to obtain a smooth, nub-free surface. Advantageously, in smoothing down the nubs not only should excess surface polymer be removed, but some of it should be used to fill the ups and downs of the thread's surface in order to obtain a sufficiently smooth undercoat structure. If this is not done, the polymer remaining on the surface follows the contours of the thread and any subsequently applied polymer coating will follow these contours.

The temperature employed in the heating oven will vary depending on the polymer components and the speed at which the thread is passed through the oven. As aforementioned, the temperatures should be raised above the melting point of the polymer of lower melting point to a level at which the polymer melts and reaches a viscosity permitting it to exude through the thread as a gelatinous mass which can then be seen on the surface of the thread when it cools. Excessively high temperatures which then the lower melting polymer to a point where it runs off should be avoided as they tend to exude too much polymer and fail to product a solid cast structure.

Regardless of the method utilized to induce the required pressure, the actual or optimum pressure applied will vary depending principally upon the particular synthetic polymer components that make up the thread, the softening conditions, the flow viscosity of the softened polymer compound and the nature of the thread construction, i.e. braid, twist, yarn, etc. It is important to note, however, that giving the thread a high level of stretch during the heating operation reduces or eliminates the necessity of applying stretch in any subsequent coating and final sizing stages that may be employed.

The optimum heating temperature employed in a softening operation wherein one of the polymer components is melted will not only depend upon the particular polymer of lower melting point employed but also on the melting point and/or the zero strength temperature of the higher melting polymeric component forming the matrix. In the case of polymers having high crystallinity, the more important consideration is not so much the melting point of the lower melting polymer but rather the temperature at which the polymer reaches a fluidity or viscosity that facilitates exudation. In the case of non-crystalline polymers, on the other hand, only the last criterion applies since non-crystalline polymers do not have a melting point. Usually this temperature is in excess of the melting point of the polymer. For example, to obtain acceptable fluidity with isotactic polypropylene which melts at about 160° C., the polymer should be heated at a temperature within the range of about 180° to 280° C. depending on its molecular weight. Fiber-forming polyethylenes will generally process in the range of about 160° to 275° C. Nylon 66 (polyhexamethylene adipamate) usually will require a heating temperature of about 280° to 295° C. and polyethylene terephthalate a heating temperature of about 270° to 320° C.

Smoothing die temperatures will also be above the melting point of the lower melting synthetic polymer and usually below the melting point of the dissimilar synthetic polymer component. In most instances, the smoothing die temperatures will conform closely to the temperature employed in the heating, i.e. structure formation/precoating stage. Preferably the smoothing die temperature about 5 to 15 degrees below that used in the structure formation/precoating stage.

In a preferred embodiment of the invention, the smooth composite suture structure formed is subjected to coating stage wherein polymer is melt extruded onto the structure. Any of the conventional extrusion apparatuses can be employed for this purpose. The smooth composite suture structure is simply fed through the extrusion coating die and coated with additional polymer of the same type as used in the structure formation, i.e. precoating stage. Optionally, a smoothing operation can follow this stage using a heated die as described above.

The extrusion temperatures employed in the coating stage depend upon the polymer added and generally will conform to those employed in the heating operation. It has also been found that when the coating is done with apparatus of the melt flow rheometer type the higher the coating temperature, other conditions being equal the greater the finished suture diameter. This is due to decreased melt viscosity with increased temperatures which results in increased polymer flow under a given applied force. The thickness of the polymer coating can be easily regulated by changing the applied extrusion force. If the coated suture is to be subjected to a final sizing operation this thickness should be 30–40 microns larger than the required final size.

After a coating stage, the coated thread preferably undergoes a final size stage. Ordinarily, a thread leaving the coating stage is thicker than the USP size limits. In order to bring it to USP size requirements, a size or calibration process is carried out. The final sizing in such cases is made by passing the coated suture through the calibration die, preferably a non-split die. In addition to its sizing function the calibration die has additional operations: (a) all possible homogeneities in the coating are eliminated (b) squeezing the coated suture through the hot calibration die results in additional co-melting of the polymer in the sheath with the polymer on the surface of the precoated thread, thus improving the adhesion of the coating to the thread and (c) if for some reason the flow rate of the polymer melt changes at extrusion during the coating stage, it results in increased thickness of the coating. The calibration die will control the final thickness by scraping off excess polymer coating.

The coated suture should contact the walls of the calibration die while still in the molten state, in order to prevent abrasion of cold polymer coating passing through the calibration die. The distance between the outlet of the coating die and the calibration die should be minimal in order to secure a coated suture which is sufficiently rigidified so that when it goes through the calibration die it takes the shape of the die but at the same time it should be soft enough to give a smooth finish. Distances of 5 to 7 cm have been found suitable. On leaving the coating die the coating thickness of the suture should be significantly larger (by 30–40 m) than the inner diameter of the calibration die in order that the space in the capillary part of the die and the entrance to the die will always be filled by the polymer melt. On the other hand, too heavy a coating will cool faster leaving the coating die and will not be heated up rapidly enough to pass through the calibration die. This will disturb the scraping action and will produce breaks in the suture or a rough surface.

When softening of the second synthetic is effected by the use of solvent, the solvent selected will depend, of course, upon the nature of the first component of thread treated since the latter must not soften during the operation. The following are illustrative of solvents generally suitable for use in softening exemplary types of synthetic polymers:

Polyesters—mixtures of halogenated hydrocarbons (e.g. methylene chloride) and halogenated alkanols (e.g. hexafluoroisopropanol).

Aromatic polyamides—strong acids and bases

Nylons—phenols

Polyolefins—aromatic hydrocarbons (e.g. xylene, toluene)

The synthetic/polymer components selected for compositing in accordance with the present invention are without limitation provided they are toxicologically acceptable, fiber- or film-forming polymers, possessing softening points sufficiently distant from each other to permit softening of one without softening or otherwise degrading the other. Thus, the synthetic polymers can be thermoplastic or non-thermoplastic polymer materials illustrative of which are homopolymers and copolymers of α olefins of 1–6 carbons, e.g. polyethylene, polypropylene, polybutene, polyisobutylene, copolymers of ethylene and propylene and the like; polyacrylates such as polymethacrylate, polyethacrylate, and the like; polyamides such as Nylon 66, i.e. poly(hexamethylene adipamide), Nylon 610, i.e. (polyhexmethylene sebacamide), Nylon 6, i.e. polycaprolactam; aromatic polyamides, such as those described in U.S. Pat. Nos. 3,063,966; 3,600,350; 3,671,542 and 3,819,587, all incorporated herein by reference, particularly poly(p-benzamide); poly(p-phenylene terephathalamide); poly(2-chloro-p-phenylene terephthalamide; poly(2,6,-dichloro-p-phenylene-2, 6-naphthalamide; poly(p-phenylene-p,p-biphenyldicarboxamide; poly(p, p'-phenylene benzamide and poly(1,5-naphthylene terephthalamide); copoly(p,p'-diaminobenzanilide terephthalamide; polyesters of difunctional carboxylic acids and diols such as polyethylene terephthalate, poly(1,4-cyclohexylene dimethylene terephthalate); polystyrene; poly(acrylonitrile); polyurethane, polyethers, polyvinyls, polypeptides such as polylactides, polyglycolides and copolymers of lactide and glycolide with each other and with other reactive monomers such as those described, for instance, in U.S. Pat. Nos. 3,636,952 and 2,683,136, incorporated by reference herein; and polymers of p-aminobenzoic acid.

Illustrative of suitable composite threads for treatment in accordance with the present invention are set forth in the following Table I:

TABLE I

| Composite | Matrix | Extruding Polymer |
|---|---|---|
| 1 | polyethylene terephthalate | isotactic polypropylene |
| 2 | Kevlar[1] | polypropylene |
| 3 | Kevlar[1] | polyethylene |
| 4 | Kevlar[1] | polyethylene terephthalate |
| 5 | chain extended polyethylene[2] | atatic polypropylene |
| 6 | Kevlar[1] | polyglycolic acid |
| 7 | Nylon 66 | isotactic polypropylene |
| 8 | Nylon 66 | polyisobutylene |
| 9 | polyethylene terephthalate | Nylon 11 |

[1] aromatic polyamide product of DuPont Corporation
[2] high strength polyolefin year having straight pull tenacity of approximately 25–50 g/denier described in Keller A. and Barham, P. J., "High Modulus Fibres", Plastics and Rubber International, Feb. Vol. 6, No. 1 (1981) incorporated herein by reference.

Figure 2:
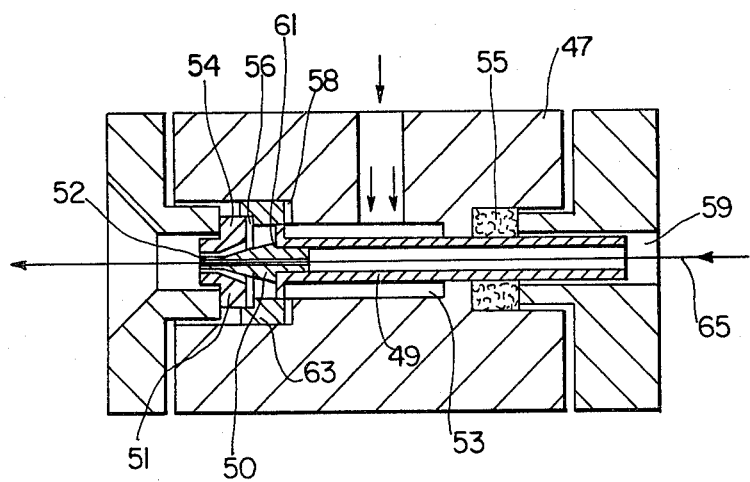

The following examples are included to further illustrate preparation of composite sutures of the invention. In the examples, reference is made to the following brief description of the drawings wherein:

FIG. 1 is a schematic drawing of an apparatus useful in the three stage melting method of the present invention and FIG. 2 is a schematic drawing in section of a spinneret useful in the extrusion coating of the formed composite suture employed in the apparatus of FIG. 1.

EXAMPLE I

Structure Formation or Precoating Stage

Directing attention to the drawings, using a conventional New England Butt braider machine polyethylene terephthalate (PET) strands of 40 denier are braided around a single core of 265 denier isotactic polypropylene to form a 4/0 raw or precursor thread with 4 ends of 40 denier PET in the cover and 1 end of 165 denier polypropylene in the core. The raw braid, wound around a reel 2, is fed through a guide 4, between nip rollers 5 about a feed roll (Godet) 6, through guide 8 into a heated 10 cm long tubular over inside Spinneret I designated 11 in FIG. 1. The lumen of Spinneret I without polyolefin feed serves this purpose, Heated Zone I in FIG. 1. A roll (Godet) 13 pulls the raw braid through the oven at a stretch ratio (SR) of 1.24. The heating oven is maintained at a temperature of 230° C. Under these conditions all the polypropylene melts and is entirely distributed throughout the braid interstices and onto the surface of the braid. No solid polypropylene core residue remains.

As the braid emerges from Spinneret I, large quantities of excess polypropylene which has melted out and formed nubs on the surface is trimmed off by a smoothing die 12 having an internal diameter (ID) of 0.180 mounted at the outlet of Spinneret I. The braid then continues through a Guide 15 to Spinneret II designated 39 which is an extrusion coating die apparatus shown in detail in FIG. 2.

Coating Stage

The smoothed precoated braid is pulled through Spinneret II by a roll (Godet) 50. Tension is let down on roll 50 so that some overfeed, i.e. a stretch ratio (SR) of approximately 0.9 is applied. Isotactic polypropylene chips are melted in heated reservoir 41 maintained at a temperature of 260° C. and the melt is forced by means of extruding weights 43 applying a force of 0.233 kg to a piston 45 into and through the tubing-type extrusion coating die apparatus 39.

Directing particular attention to FIG. 2, the extruding coating apparatus 39 is comprised of a holder indicated generally as 47 which houses a hollow guide tube 49 and a die holder 50 which retains a die 51. Die 51 has an outlet 52. The guide tube 49 is essentially positioned within the holder 47 so as to provide an annular chamber 53. A Teflon gasket 55 seals one end of the guide tube 49 within the holder while the other end is connected to die 51 and sealed by aluminum gaskets 54, 56 and 58. The guide tube contains an inlet 59 and an outlet 61. Between outlet 61 and outlet 52 of the die 51 is positioned a hollow needle 63. The polypropylene melt from heated reservoir 41 is forced by piston 45 through channel 65, into annular chamber 53 and over needle 63. The impregnated/precoated thread 65 passes consecutively through guide tube 49, hollow needle 59, outlet 52 and is coated with the melt as it emerges from the due 51. The coating die is maintained at a coating temperature of 230° C.

Final Sizing or Calibration Stage

The coated thread is passed to a Spinneret III designated 66 whose design is like that of Spinneret I except that a calibration die 67 (see FIG. 1) having an internal diameter of 0.220 mm is employed so as to provide a finished 4/0 suture. Spinneret III is positioned approximately 5 cm from the outlet of Spinneret II so as to provide a coated thread cooled to a rigidity that allows the coated thread when it enters Spinneret III to take the shape of calibration die 67 but is soft enough to give a smooth finish. The working temperature of Spinneret III is 220° C. Some overfeed (Stretch Ratio, SR approximately 0.9) is applied in the finishing stage as in the coating stage so as to improve the smoothness of the final product.

The finished suture is finally wound around receiving reel 69 and identified in the Table II below as CK suture 4-0.

Sutures of 3-0, 5-0 and 6-0 diameter size were similarly prepared and the mechanical properties of these sutures, identified below as CK sutures 3-0, 5-0 and 6-0 as well CK Suture 4-0 are reported in Table II. Also included for purposes of comparison are the mechanical properties of commercial sutures of like size.

knot values 50-60% higher than CK Sutures of the same size. For PET Braid Suture 4-0 and 5-0 the difference is about 20%.

Gurley Stiffness

By comparing all materials having the same 3-0 size (samples 1-5, all of them monofilaments) it is seen that the CK Suture 3-0 has the lowest Gurley Stiffness (G.S.). Size 3-0 polypropylene monofilaments (Prolene from ethicon and PP from Thiokol) and nylon monofilament (from Deknatel) have G.S. 2.5-3 times higher than that of similarly sized CK Suture. PET 3-0 monofilament has the highest G.S. —6.3 times higher than that of the CK Suture.

When comparing G.S. of size 4-0 materials (samples 6-10) it can be seen that the G.S. of Prolene 4-0 is still remarkably higher (by 68%) than that of the KC Suture but, on the other hand, the G.S. of PET 4-0 multifilament suture from Deknatel is two times lower than that of CK Suture 4-0. Such a result is not surprising when comparing the stiffness of multifilament with monofilament yarns.

In the size 5-0 the G.S. of CK Suture is 39% lower than that of Prolene, but 3.9 times higher than that of PET 5-0 multifilament.

TABLE II

| No. | Type of Suture | Knot-pull Tensile Strength, $F_{knot}$ (g) Required by USP* | Knot-pull Tensile Strength, $F_{knot}$ (g) Measured | Percent Elongation (%) | Knot Security $K_{sec}$ | Knot Security $n_{ksec}$—1/5 | Gurley Stiffness G.S. (mg) |
|---|---|---|---|---|---|---|---|
| 1 | CK Suture 3-0 | 1200 | 1456 | 15.0 | 2 | — | 8.2 |
| 2 | Prolene 3-0 (from Ethicon) | " | 1504 | 58.3 | 3 | $n_2/5 = 5$ | 19.8 |
| 3 | PP Yellow Monofil. 3-0 (from Thiokol) | " | 1430 | 39.4 | 3 | $n_2/5 = 5$ | 24.9 |
| 4 | Nylon White Monofil. 3-0 (from Deknatel) | " | 1434 | 50.4 | 4 | $n_3/5 = 5$ | 22.8 |
| 5 | PET Monofil. 3-0 | " | 2430 | 76.1 | 3 | $n_2/5 = 5$ | 52.0 |
| 6 | CK Suture 4-0 | 750 | 930 | 12.8 | 2 | — | 5.9 |
| 7 | Prolene 4-0 (from Ethicon) | " | 946 | 56.7 | 3 | $n_2/5 = 5$ | 9.9 |
| 8 | PP Blue Monofil. 4-0 | " | 841 | 29.1 | 3 | $n_2/5 = 5$ | 14.4 |
| 9 | Nylon White Monofil. 4-0 (from Deknatel) | " | 950 | 47.8 | 4 | $n_3/5 = 5$ | 12.6 |
| 10 | PET Green Braid Suture 4-0 | " | 1146 | 16.5 | 4 | $n_3/5 = 1$ | 3.0 |
| 11 | CK Suture 5.0 | 500 | 649 | 14.2 | 2 | — | 2.2 |
| 12 | Prolene 5-0 (from Ethicon) | " | 646 | 44.9 | 3 | $n_2/5 = 5$ | 3.1 |
| 13 | PP Blue Monofil. 5-0 | " | 532 | 31.5 | 3 | $n_2/5 = 3$ | 5.9 |
| 14 | Nylon White Monofil. 5-0 (from Deknatel) | " | 577 | 51.0 | 4 | $n_3/5 = 5$ | 5.4 |
| 15 | PET Green Braid Suture 5-0 (from Deknatel) | " | 770 | 25.2 | 4 | $n_3/5 = 1$ | 0.6 |
| 16 | Suture 6-0 | 250 | 318 | 11.0 | 2 | — | 0.4 |
| 17 | Prolene 6-0 (from Ethicon) | " | 270 | 50.0 | 3 | $n_2/5 = 4$ | 0.6 |
| 18 | PP Blue Monofil. 6-0 | " | 192 | 29.9 | 3 | $n_2/5 = 5$ | 1.1 |
| 19 | PET Monofil. 6-0 | " | 485 | 37.0 | 3 | $n_2/5 = 5$ | 3.3 |

*The limits on $F_{knot}$ apply to non-sterile sutures.

RESULTS

Knot-Pull Tensile Strength

Sizes 3-0, 4-0 and 5-0 CK Sutures have the same F knot as Prolene and Nylon Monofilaments (the differences being within the limits of 3% except for Nylon 5-0 which is 12% weaker than CK Suture 5-0). It should be noted that the values of 5-0 sutures are 20-30% higher than required by U.S.P. In size 6-0 the F knot of the CK Suture is 18% higher than that of Prolene. PP monofilament (blue) is remarkably weaker than the CK Suture (the difference increases from 11% in size 4-0 up to 66% in size 6-0).

PET sutures have F knot values higher than CK Sutures. PET Monofilaments of 3-0 and 6-0 have F It may be safely stated that, when comparing CK Suture with other sutures of the same size, the G.S. of CK Sutures is remarkably lower than that of Prolene, PP, PET and Nylon monofilaments. This difference is particularly high when comparing with PET monofilaments of the same size. On the other hand, the G.S. of CK Sutures is remarkably higher than that of PET multifilament sutures. This results from the structure of CK Sutures.

Elongation

The P.E. of CK Sutures of all sizes varies from 11% to 15%. The P.E. of other monofilament sutures is much higher, for example: P.E. of Prolene in all sizes varies from 45% to 58%; of PP monofilament from 29% to 39%; of Nylon monofilament from 41% to 51%; and of PET monofilament from 37% to 76%. Only P.E. of PET multifilament suture 4-0 (16.5%) is close to the desired value.

Knottability

Knottability results show that the CK Suture has the lowest stiffness and elongation when compared with other monofilament sutures. It can, therefore, be stated on the basis of these two quantitative parameters, that the knottability of the CK Suture is better than that of any other monofilament suture.

Knot Security

It may be seen from the Tables that all investigated materials can be divided into 3 groups with corresponding $k_{sec}=2;3$ and 4. CK Sutures belong to the group with $k_{sec}=2$. All Prolene sutures, PP monofilaments and PET monofilaments belong to the second group with $k_{sec}=3$. PET braids and nylon monofilaments belong to the third group with $k_{sec}=4$. It means that with CK Sutures, a secure knot can be tied using only two throws Square Knot. All other investigated materials need at least one additional throw for secure knot formation and nylon monofilaments and PET braids need even two additional throws.

Microscopic examination (250×) of a cross-section of the finished suture shows virtually no dead spaces present. The finished suture is free of stripping and cracking and possesses the smoothness of a monofilament.

In commercial production, needles may be attached to one end of the composite sutures of the invention and the sutures may be packed in sterile containers. Inasmuch as the sutures are stable for long periods of time without a conditioning fluid, the sutures may be dry packed in glass tubes or plastic envelopes. Conditioning fluid may be used to assure maintenance of sterility or as a rule preventing medium for the needle. Eyeless needles are preferred since they cause less tissue damage. Conveniently, the composite sutures of the present invention are formed at convenient lengths, attached to eyeless needle, wound on reels if desired, and placed in containers such as plastic envelopes. The sutures may then be sterilized with ethylene oxide or other conventional gaseous sterilizing agents in accordance with known practices. Alternatively, the sutures may be sealed in the envelopes and then sterilized by using heat and radiation including x-rays, gamma rays, electrons, neutrons, etc.

EXAMPLES II–IX

Example I is repeated using the following synthetic materials as the matrix and core, i.e. lower melting point component and conducting the heating in Heating Zones I and II as indicated.

| Example | Matrix | Core | Spinneret I, °C. | Spinnerette II & III, °C. |
|---|---|---|---|---|
| II | Kelvar[1] | isotactic polypropylene | 220 | 220 |
| III | Kevlar[1] | polyethylene | 225 | 220 |
| IV | Kevlar[1] | polyethylene terephthalate | 265 | 265 |
| V | chain extended polyethylene[2] | atactic polypropylene | 70 | 65 |
| VI | Kevlar[1] | polyglycolic acid | 238 | 230 |

-continued

| Example | Matrix | Core | Heating Zone I, °C. | Heating Zone II, °C. |
|---|---|---|---|---|
| VII | Nylon 66 | istotactic polypropylene | 230 | 222 |
| VIII | Nylon 66 | polyisobutylene | 200 | 190 |
| IX | polyethylene terephthalate | Nylon 11 | 237 | 237 |

(1) } See Table I, supra
(2) }

It is claimed:

1. A method of preparing a surgical suture comprising forming a thread having interstices therein, comprised of a plurality of fibers of a first synthetic polymer, said thread further comprising second synthetic polymer in intimate association with and present along the length of at least one of said plurality of fibers, said second synthetic polymer having a lower melting point than said first synthetic polymer, heating the thread to a temperature sufficient to liquify the second synthetic polymer but not the first synthetic polymer to cause flow thereof, placing the thread under tension during said melting to compress the thread and redistribute the liquified second polymer throughout the plurality of fibers of said first synthetic polymer so as to substantially fill the interstices of said thread, said liquified polymer being present during said redistribution in an amount sufficient to exude through the interstices of the unmelted fibers and onto the surface of the thread to form a coating thereon and to form an internal cast extending throughout said thread, said internal cast forming an anchor onto which additional second synthetic polymer can be secured, if desired, and sterilizing the resulting thread to form a surgical suture.

2. A method according to claim 1 wherein the second synthetic polymer is in fiber form.

3. A method according to claim 1 wherein the first synthetic polymer is aromatic polyamide.

4. A method according to claim 3 wherein the aromatic polyamide is poly(p-phenylene terephthalamide).

5. A method according to claim 3 wherein the aromatic polyamide is poly(1,4-benzamide).

6. A method according to claim 1 wherein the first symthetic polymer is chain extended, polyethylene having a straight pull tenacity of about 30 to 50 grams/denier.

7. A method according to claim 3 wherein the first synthetic polymer is polyester.

8. A method according to claim 7 wherein the polyester is polyethylene terephthalate.

9. A method according to claim 1 wherein the second synthetic polymer is polyolefin.

10. A method according to claim 9 wherein the polyolefin is polyethylene.

11. A method according to claim 9 wherein the polyolefin is polypropylene.

12. A method according to claim 1 wherein said coating is subjected to smoothing.

13. A method according to claim 12 wherein said smoothing is effected by passing the composite after said heating through a heated smoothing die.

14. A method according to claim 1 wherein the composite formed is coated with the same synthetic polymer as said second synthetic polymer.

15. A method according to claim 14 wherein the coated composite is subjected to smoothing.

16. A method according to claim 15 wherein said smoothing is effected by passing the composite after said heating through a heated smoothing die.

17. A method according to claim 1 wherein the second synthetic polymer comprises at least one fiber.

18. A method according to claim 17 wherein the second synthetic polymer is polyolefin.

19. A method according to claim 18 wherein the polyolefin is polypropylene.

20. A method according to claim 19 wherein the polyolefin is polypropylene.

21. A method according to claim 1 wherein the first synthetic polymer is a polyamide terephthalate.

22. A method according to claim 21 wherein the polyamide is aromatic polyamide.

23. A method according to claim 22 wherein the aromatic polyamide is poly(p-phenylene terephthalamide).

24. A method according to claim 22 wherein the aromatic polyamide is poly(1,4-benzamide).

25. A method according to claim 21 wherein the polyamide is poly(hexamethylene adipamide).

26. A method according to claim 21 wherein the polyamide is polycaprolactam.

27. A method according to claim 21 wherein the polyamide is poly(hexamethylene sebacamide).

28. A method according to claim 20 wherein the polyamide is poly(w-aminoundecanoic acid).

29. A method according to claim 1 wherein the first synthetic polymer is polyester.

30. A method according to claim 29 wherein the polyester is polyethylene terephthalate.

31. A method according to claim 1 wherein the first synthetic polymer is extended polyethylene having a straight pull tenacity of about 30 to 50 grams/denier.

32. A method according to claim 1 wherein the first synthetic polymer is polypropylene, the second synthetic polymer is polyethylene terephthalate and the softening achieved by heating the composite to a temperature of about 180° to 280° C.

33. A method according to claim 1 wherein the first synthetic polymer is polyethylene terephthalate the second synthetic polymer is polyethylene and the softening is achieved by treating to a temperature of about 160° to 275° C.

* * * * *